United States Patent
Maiwald

[11] Patent Number: 6,096,943
[45] Date of Patent: Aug. 1, 2000

[54] SKIN WOUND PROTECTOR

[76] Inventor: Diane C Maiwald, 12 Vannina Pl., Huntington, N.Y. 11743

[21] Appl. No.: 09/026,996

[22] Filed: Jan. 9, 1998

[51] Int. Cl.⁷ ..................................................... A61F 13/00
[52] U.S. Cl. ............................................... 602/48; 602/54
[58] Field of Search ........................ 602/41–59; 128/846, 128/888, 889, 893, 894; 428/195, 47, 71, 76, 88, 97, 99; 604/305, 306, 307, 308; 424/443, 445, 446, 447, 448, 449

[56] References Cited

U.S. PATENT DOCUMENTS

| | | | |
|---|---|---|---|
| 2,273,873 | 2/1942 | Klein | 128/888 |
| 2,442,140 | 6/1948 | Larsen | 128/888 |
| 4,117,841 | 10/1978 | Perrotta . | |
| 4,460,370 | 7/1984 | Allison et al. . | |
| 4,624,665 | 11/1986 | Nuwayser . | |
| 4,645,502 | 2/1987 | Gale et al. . | |
| 4,655,767 | 4/1987 | Woodard et al. . | |
| 4,810,499 | 3/1989 | Nuwayser . | |
| 4,812,305 | 3/1989 | Vocal . | |
| 4,849,224 | 7/1989 | Chang et al. . | |
| 4,858,604 | 8/1989 | Konishi . | |
| 4,879,119 | 11/1989 | Konno et al. . | |
| 4,907,579 | 3/1990 | Kum . | |
| 5,144,958 | 9/1992 | Krueger et al. | 128/888 X |
| 5,330,452 | 7/1994 | Zook | 602/48 X |
| 5,395,675 | 3/1995 | Altholtz et al. | 428/195 |
| 5,495,856 | 3/1996 | Fentress | 128/846 |
| 5,780,048 | 7/1998 | Lee | 424/443 |
| 5,891,463 | 4/1999 | Bello et al. | 424/449 |

Primary Examiner—Kim M. Lee
Attorney, Agent, or Firm—Michael I. Kroll

[57] ABSTRACT

The present invention relates to a skin wound protector (14). The skin wound protector (14) protects a wound (12) from contact with solid objects and includes a substantially planar peripheral region (18) having top and bottom sides with adhesive (17) on the bottom for securing the protector to an area surrounding the wound, and a deformable interior region (16) which rises above the peripheral region (18) top side to form a hollow cavity such that, when the adhesive is secured to the area surrounding the wound, the wound resides within the cavity and is isolated from contact by solid objects. The protector can be of unitary or multiple-piece construction and can fabricated out of air-permeable, air-impermeable, clear or opaque plastic. The hollow cavity is generally dome-shaped and can further contain a medicating fluid (13) for treating the wound.

1 Claim, 2 Drawing Sheets

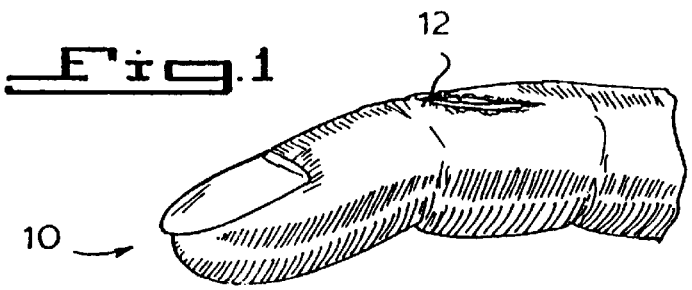
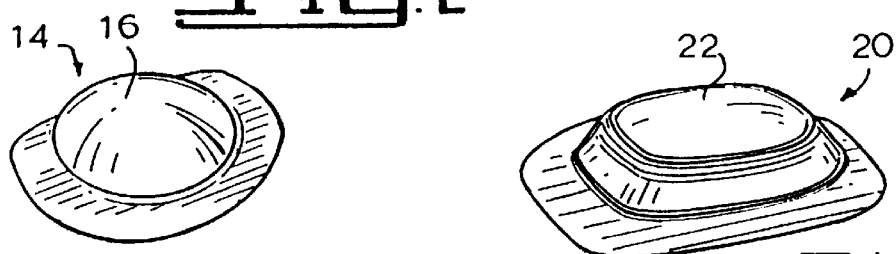
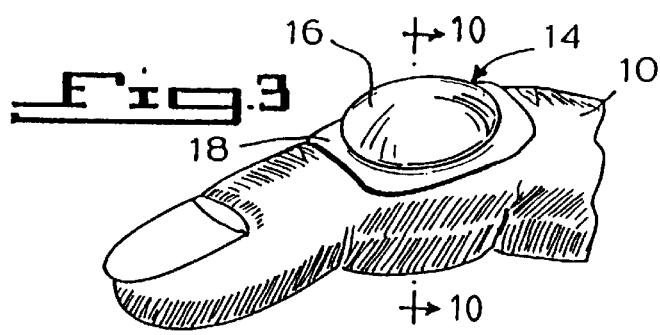
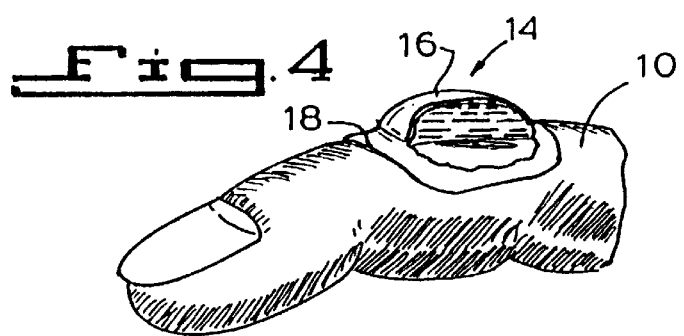

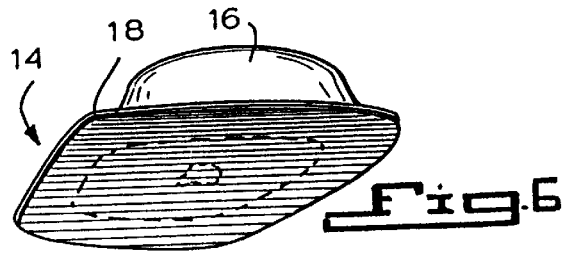
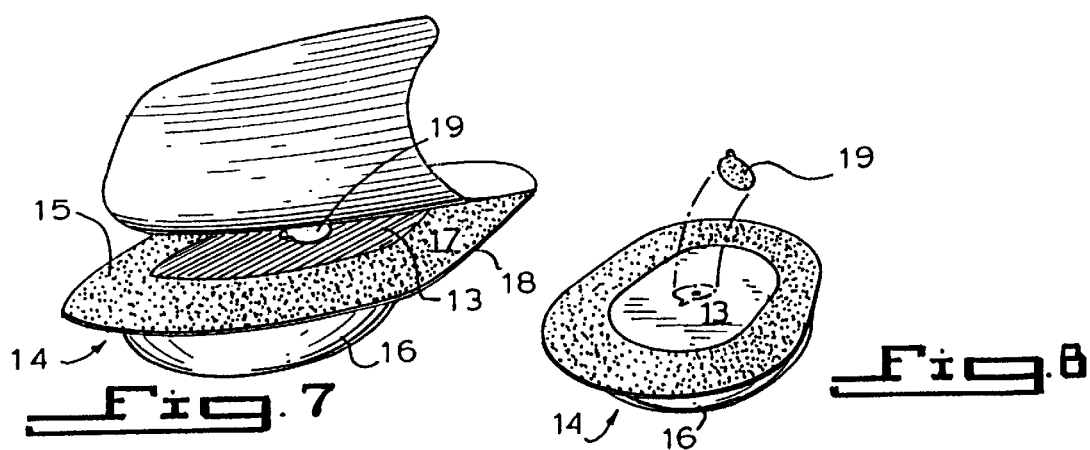
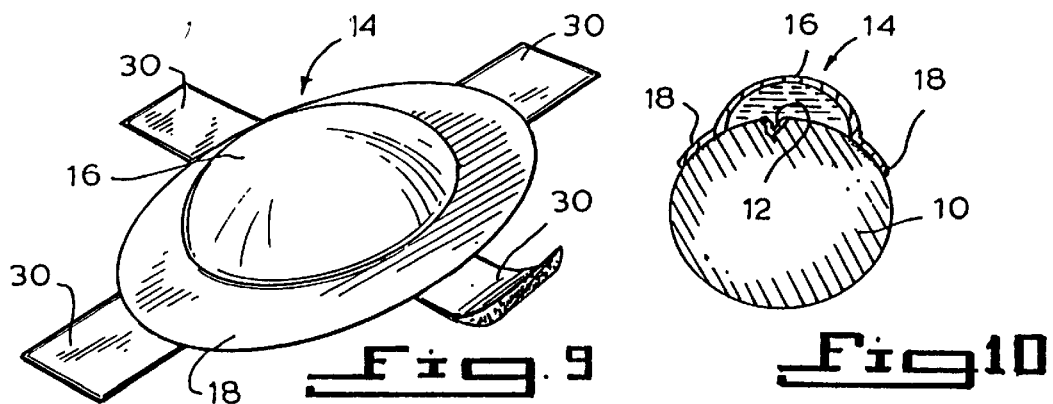

SKIN WOUND PROTECTOR

BACKGROUND OF THE INVENTION

1. Field of the Invention

The present invention relates to an improved skin wound protector. More particularly, the present invention relates to a skin wound protector for protecting, or shielding, an area or wound of a person from irritation by means of a "bubble" or dome-shaped space above the area or wound. With the protector of the present invention, the wound is not contacted by the protective shield and stress that impinges on the shield is resisted, diffused and absorbed by this "bubble" or dome-shaped space and not by the wound itself. This bubble or dome-shaped space is generally filled with air. Other variations include filling the "bubble" or dome-shaped space with a medicament that would become fluid, e.g., a gel or ointment. The term fluid is to be taken as referring to air as well as these alternate liquids.

Additionally, the present invention is capable of delivering a measured amount of medication for aiding in the healing of such wound.

2. Description of the Prior Art

Protective devices for skin wounds are known in the art, and generally include so-called adhesive strip protectors for the protection of one's cuts and bruises. Such adhesive strip protectors are commercially available, for example, under the well-known trademark of "Band-Aid" by Johnson & Johnson. Such common adhesive strips either, in whole or in part, stick directly to one's cut or bruise or, in some manner, rub against and irritate one's wound.

U.S. Pat. No. 4,117,841 (Perrotta, A. et al., Oct. 3, 1978) discloses a conventional adhesive bandage which lies directly over the wound, modified to contain a rupturable pocket containing a suitable medicament.

U.S. Pat. No. 4,460,370 (Allison, K. C. et al., Jul. 17, 1984) discloses a transdermal medication application cell utilizing a medication-permeable membrane which lies directly over the skin of the person being treated.

U.S. Pat. No. 4,812,305 (Vocal, R. S., Mar. 14, 1989) discloses an adhesive bandage having a foam well for holding medication and for preventing irritation of the wound.

U.S. Pat. No. 4,858,604 (Konishi, R., Aug. 22, 1989) discloses a conventional adhesive bandage which lies directly over the wound, modified to contain a rupturable capsule containing a suitable medicament.

Numerous innovations for bandages have been provided in the prior art that are adapted to be used. Even though these innovations may be suitable for the specific individual purposes to which they address, they would not be suitable for the purposes of the present invention as heretofore described.

BRIEF SUMMARY OF THE INVENTION

It is an object of the present invention to provide an improved skin wound protector which will fulfill the needs heretofore recognized and lacking in the prior art.

It is a further object of the present invention to provide an improved skin wound protector which will reduce, if not eliminate, stress forces which impinge upon the wound of a person thereby causing further irritation to the wound.

It is another object of the present invention to provide an improved skin wound protector which will permit the safe and effective delivery of medication to the wound of a wearer of the present invention.

It is an additional object of the present invention to provide an improved skin wound protector which is both economical to manufacture and may be offered for sale at a competitive price.

The foregoing and related objects are accomplished by an improved skin wound protector which includes the provision of a gap, or bubble, existing immediately above the wound of the wearer of the protector in order to reduce, if not totally eliminate, the effect of stress forces against the wound which would otherwise impinge on the wound and cause irritation.

The gap or bubble created by the wound protector of the present invention should be formed out of a sufficiently deformable material which would withstand contact with other objects via deformation of the bubble. It should resist, diffuse, and/or absorb the force of contact throughout the non-adhesive portion of the skin wound protector and the surrounding adhesive area, thereby isolating the wound itself from such contact.

In addition, and in a preferred embodiment of the present invention, the wound protector would be provided with means for the delivery of a medication fluid from a point immediately above, but preferably not touching, the wound of the person wearing the wound protector. The medicating fluid would preferably be contained in a separate compartment, enclosed with a removable seal, which can be readily removed by the wearer when the wound protector of the present invention is ready for use.

Furthermore, the dome-shaped portion of the protector of the present invention can be suitably made so as not to include any sharp edges and, further, can be made to be capable of elongation.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 is a perspective view of a finger of a person with a wound therein.

FIG. 2 is a top perspective view of the skin wound protector of the present invention.

FIG. 3 is a perspective view of the skin wound protector, as shown in FIG. 2, covering a wound of a person's finger, as shown in FIG. 1.

FIG. 4 is a perspective view of the skin wound protector, as shown in FIG. 3, with the wound protector being shown partially cutaway.

FIG. 5 is a top perspective view of an alternative, preferred embodiment of the skin wound protector of the present invention.

FIG. 6 is a bottom perspective view of the skin wound protector of the present invention, prior to use.

FIG. 7 is a perspective view of the underside of the skin wound protector of FIG. 6, showing the partial removal of a covering for the adhesive means for securing the wound protector to cover a wound of a wearer.

FIG. 8 is a perspective view of the underside of the skin wound protector of FIG. 7, following the complete removal of the covering of the adhesive means for securing the wound protector, as well as the removal of a separate seal for allowing the passage of medicating fluid from a closed compartment onto the wound of a wearer of the present invention.

FIG. 9 is a top perspective view of an alternative embodiment of the present invention with a particularly preferred embodiment with respect to the means for the securement of the skin wound protector to the skin, e.g., finger, of a wearer.

FIG. 10 is a cross sectional view, taken in elevation, of the skin wound protector of the present invention, as shown in FIG. 3, taken along the 10—10 line of FIG. 3.

DETAILED DESCRIPTION OF THE PREFERRED EMBODIMENTS

Turning now descriptively to the drawings, in which similar reference characters denote similar elements throughout the several views, the Figures illustrate a skin wound protector of the present invention. With regard to the reference numerals used, the following numbering is used throughout the various drawing figures.

10 finger of the wearer
12 wound in 10
13 medicating fluid
14 skin wound protector
15 lower surface of 14
16 deformable dome-shaped portion of 14
22 rectangular raised portion
17 adhesive means
18 planar portion of 14
19 seal
20 alternative, preferred embodiment of 14
30 means for the securement of 14 to the skin Turning now in detail to an analysis of the accompanying drawing figures, FIG. 1 is a perspective view of a finger 10 of a person with a wound 12 therein.

FIG. 2 is a top perspective view of the skin wound protector of the present invention. Wound protector 14 includes a dome-shaped portion 16, preferably made out of a deformable material, such as a plastic, which can withstand forces which would otherwise rub against a conventional wound protector, such as an adhesive strip, and thus cause additional irritation to the wound or abrasion.

Planar portion 18, as will be explained in greater detail, includes adhesive means, on the underside portion of that shown in FIG. 2, and as will be discussed in greater detail, particularly in connection with FIG. 7.

FIG. 3 is a perspective view of the skin wound protector 14, as shown in FIG. 2, covering the wound of a person's finger 10, as shown in FIG. 1. Wound protector 14 is secured to the skin of finger 10 by the provision of adhesive means on the underside of planar portion 18.

FIG. 4 is a perspective view of the skin wound protector 14, as shown in FIG. 3, with the wound protector being shown partially cutaway. Dome-shaped portion 16 is shown as being able to contain either a medicating fluid or air. The dome shape of portion 16 is to be designed to absorb the shock of forces which would otherwise irritate a wound with a conventional wound protector.

FIG. 5 is a top perspective view of an alternative, preferred embodiment of the skin wound protector 20 of the present invention. This embodiment of the present invention has a more rectangular-raised portion 22 than the embodiment shown in FIGS. 2 through 4. However, like the embodiment of FIGS. 2 through 4, this embodiment includes a planar portion 18, the underside of which is provided with adhesive means, and further, includes no sharp or pointed edges, which might further be able to irritate one's cut or wound.

FIG. 6 is a bottom perspective view of the skin wound protector of the present invention, prior to use. FIG. 7 is a perspective view of the underside of the skin wound protector of FIG. 6, showing the partial removal of a covering for the adhesive means for securing the wound protector to cover a wound.

The lower surface 15 of the wound protector 14 is to be substantially planar, prior to use, and capable of conforming to the skin of the user of the present invention. As shown in FIG. 6, prior to use, lower surface 15 has a protective covering, as illustrated by the horizontal shading of the same.

As shown in FIG. 7, this protective covering is partially removed, and prior to use, such covering is fully removed by the user in order to expose adhesive means 17, which is on the underside of planar portion 18.

As discussed heretofore, a portion of dome-shaped portion 16 may, optionally, be filled with a medicating fluid 13. In order to release such fluid for use upon the wound, seal 19 is removed, as best shown in FIG. 8.

FIG. 9 is a top perspective view of an alternative embodiment of the present invention with a particularly preferred embodiment with respect to the means for the securement of the skin wound protector to the skin, e.g., finger, of a wearer. In the embodiment of FIG. 9, a preferred, four-way adhesive means for securement of the present invention to the skin of a wearer is shown.

FIG. 10 is a cross sectional view, taken in elevation, of the skin wound protector of the present invention, as shown in FIG. 3, taken along the 10—10 line of FIG. 3.

The skin wound protector protects a skin wound from contact with solid objects by utilizing a design having a substantially planar peripheral region having top and bottom sides; adhesive on the bottom side of the peripheral region for securing the wound protector to an area immediately surrounding the wound; and a deformable interior region which rises above the planar peripheral region top side to form a hollow cavity such that, when the peripheral region bottom side is secured to the area surrounding the wound, the wound resides within the cavity and is accordingly isolated from contact by solid objects. It can be readily appreciated that the deformable interior be manufactured from a readily deformable material, and that, by virtue of its forming a closed, sealed cavity over the wound, the air pressure inside the hollow cavity will act to provide additional structural strength to the cavity. Preferably, the interior region is fabricated out of plastic.

With regard to the plastic used, there are certain uses wherein it would be advantageous for the plastic to be air-permeable, such that the wound remains relatively aerated, while for other applications, it would be advantageous for the plastic to be air-impermeable. Accordingly, the interior region of the wound protector can be suitable fabricated out of either air-permeable or air-impermeable material. One preferred embodiment of the invention utilizes a clear plastic. so that the wound can be monitored during the healing process.

With regard to the manufacture of the invention, one embodiment utilizes a unitary article, formed out of a single piece of material, with adhesive applied to the bottom portion of the planar peripheral region. This leads to high structural integrity, in addition of ease and cost of manufacture advantages. Alternatively, the article can be formed of a plurality of components which are then affixed together to produce the invention.

It will be understood that each of the elements described above, or two or more together, may also find a useful application in other types of applications differing from the type described above.

While the invention has been illustrated and described as embodied in a skin wound protector, it is not intended to be limited to the details shown, since it will be understood that various omissions, modifications, substitutions and changes in the forms and details of the formulation illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims.

What is claimed is:

1. A skin wound protector for protecting a skin wound from contact with solid objects, comprising:

a) a substantially planar peripheral region having top and bottom sides;

b) adhesive on said bottom side of said peripheral region for securing said skin wound protector to an area surrounding the skin wound;

c) a dome shaped substantially spherical deformable fully enclosed housing of clear plastic material having an interior region which rises above said peripheral region top side to form a hollow closed and sealed cavity over the skin wound and having means comprising air pressure within said cavity to provide structural strength to said cavity such that, when said peripheral region bottom side is secured to an area surrounding a skin wound, the skin wound resides within said cavity and is isolated from contact by solid objects; and d) a portion of said cavity filled with a medicating fluid having a removable seal for releasing said medicating fluid into said hollow cavity upon removal of said seal.

* * * * *